United States Patent [19]
Singer et al.

[11] Patent Number: 5,484,394
[45] Date of Patent: *Jan. 16, 1996

[54] METHOD AND APPARATUS FOR ROTATING A WRIST

[75] Inventors: Robert D. Singer, Clive; Ernest A. Trickey, Des Moines, both of Iowa

[73] Assignee: ElectroBionics Corporation, Des Moines, Iowa

[*] Notice: The term of this patent shall not extend beyond the expiration date of Pat. No. 5,219,323.

[21] Appl. No.: 76,111

[22] Filed: Jun. 14, 1993

Related U.S. Application Data

[63] Continuation-in-part of Ser. No. 718,774, Jun. 21, 1991, Pat. No. 5,219,323.

[51] Int. Cl.⁶ .................................................. A61F 5/00
[52] U.S. Cl. ........................... 602/16; 602/20; 602/21
[58] Field of Search ................................. 602/5, 16, 20, 602/21, 23–27, 29; 128/881; 623/57, 59, 61; 482/94, 139; 601/23, 33

[56] References Cited

U.S. PATENT DOCUMENTS

| | | | |
|---|---|---|---|
| 43,596 | 7/1864 | Koeller | 623/61 X |
| 2,135,018 | 11/1938 | Svensson | 482/94 |
| 2,542,316 | 2/1951 | Farrar, Jr. | 623/61 |
| 2,626,398 | 1/1953 | Grindle et al. | 623/57 |
| 2,767,708 | 10/1956 | Keropian | 602/21 |
| 3,089,700 | 5/1963 | Hotas | 482/94 |
| 3,683,897 | 8/1972 | Shield et al. | |
| 3,707,963 | 1/1973 | Keropian | 602/21 |
| 4,237,873 | 12/1980 | Terry et al. | 602/20 |
| 4,433,679 | 2/1984 | Mauldin et al. | 602/20 X |
| 4,538,595 | 9/1985 | Hajianpour | |
| 4,559,932 | 12/1985 | Salort | 602/20 |
| 4,612,919 | 9/1986 | Best | 602/16 |
| 4,651,719 | 3/1987 | Funk et al. | 602/20 X |
| 4,669,451 | 6/1987 | Blauth et al. | |
| 4,809,688 | 3/1989 | Aymerica del Valle et al. | 602/21 |
| 5,002,044 | 3/1991 | Catler | 602/21 X |
| 5,117,814 | 6/1992 | Lattrell et al. | |

*Primary Examiner*—Linda C. Dvorak
*Attorney, Agent, or Firm*—Schwartz & Weinrieb

[57] ABSTRACT

Apparatus and methods of rotating a non-functioning or injured wrist by flexing or extending the associated elbow may be activated by muscle action of the wearer or by an elbow actuator. Cuffs disposed above and below the elbow that receive the wrist and arm are interlinked in a manner that permits varying of the degree of supination and pronation of the wrist to the needs of the wearer. Also, the angle of elbow flexion at which wrist rotation starts and stops can be varied by adjusting the operating mechanism.

27 Claims, 11 Drawing Sheets

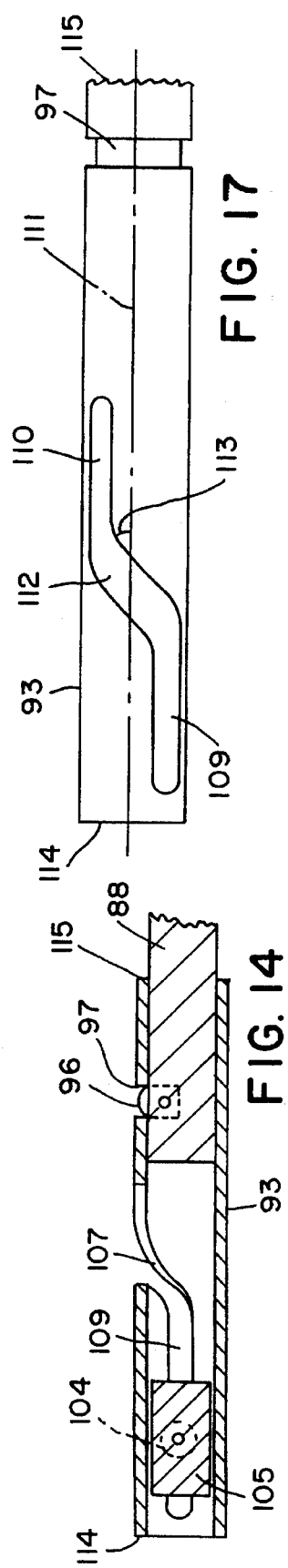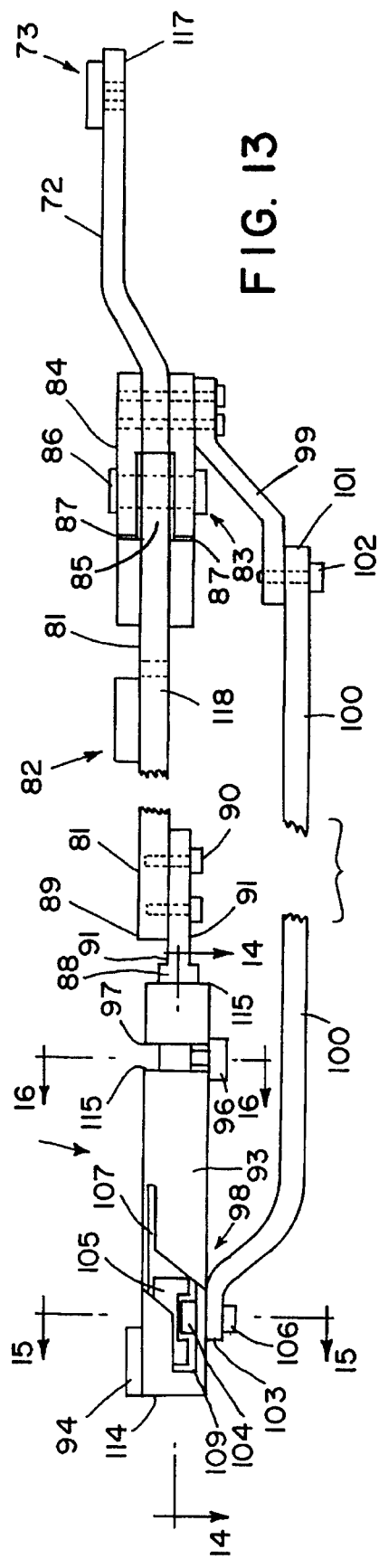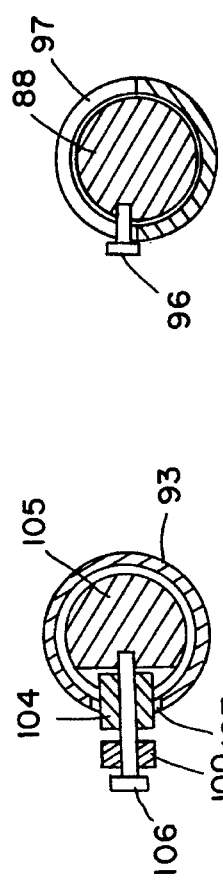

1

METHOD AND APPARATUS FOR ROTATING A WRIST

RELATED INVENTIONS

This application is a continuation-in-part of Application for U.S. patent Ser. No. 07/718,774, filed Jun. 21, 1991, now U.S. Pat. No. 5,219,323.

BACKGROUND OF THE INVENTION

This invention relates to orthotic and rehabilitative rotation of the human wrist, and more particularly, to methods and apparatus that rotate a wrist to varying degrees depending on the amount of flexion of the associated elbow.

Equipment used for rotating human wrists in the past has been complicated and cumbersome. Some of these devices have substituted spring mechanisms for human muscles. These systems provide either inward (pronation) or outward (supination) rotation, but not both. Other devices such as those shown in U.S. Pat. No. 5,117,814, require rotation of a threaded cable to cause flexing and extension of a joint. Also, clothing can not be worn over orthotic equipment and therapy equipment when it is large and bulky or when the clothing could become entangled in the moving parts.

OBJECTIVES OF THE INVENTION

Accordingly, it is an object of this invention to provide improved methods and apparatus for rotating a human wrist.

Another object of this invention is to provide easily adjustable and customizable methods and apparatus for turning a wrist.

A further object is to provide wrist rotating methods and apparatus that permit functional use of a paralyzed wrist and can provide controlled therapeutic pronation/supination continuous passive motion for rehabilitating an arm or wrist following surgery or trauma.

Another object is to provide wrist rotation apparatus that encapsulates a significant area of the arm yet is small enough to fit under a loose fitting shirt.

An additional object is to provide methods and apparatus that smoothly articulate a wrist to a predetermined degree of inward or outward rotation as a person flexes or extends the elbow.

Another object is to provide wrist rotation methods and apparatus that may be powered either by a person flexing or extending an elbow, or by an electronic elbow actuator controlled by such a person.

A further object is to provide wrist rotation apparatus and methods that enable a person lacking a functional wrist to perform activities of daily living, such as combing hair, feeding themself, and shaving both sides of the face.

An additional object is to provide relatively simple and low cost, durable, easily maintained wrist rotating apparatus and methods that are portable and can be easily attached and removed, and which do not possess defects found in similar prior art devices and methods.

Other objects and advantages of the invention will be found in the specification and claims, and the scope of the invention will be set forth in the claims.

DESCRIPTION OF THE DRAWING

FIG. 13 is an enlarged, partial top plan view of the apparatus shown in FIG. 12 with parts broken to save space.

FIG. 14 s an enlarged cross-sectional view taken along the line 14—14 in FIG. 13.

FIG. 15 is an enlarged cross-sectional view taken along the line 15—15 in FIG. 13.

FIG. 16 is an enlarged cross-sectional view taken along the line 16—16 in FIG. 13.

FIG. 17 is an enlarged top plan view of the tube.

DESCRIPTION OF THE INVENTION

Figure 1:
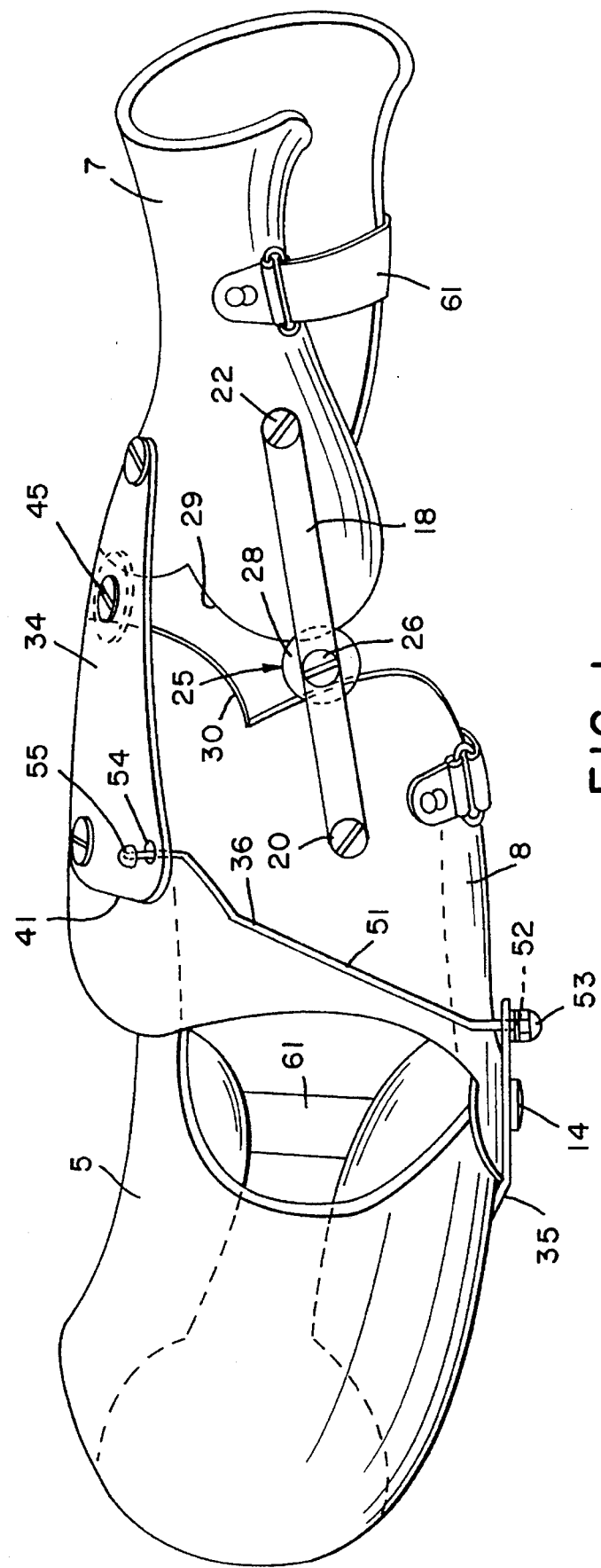
FIG. 1 is a perspective view of the apparatus in accord with this invention.
Figure 2:
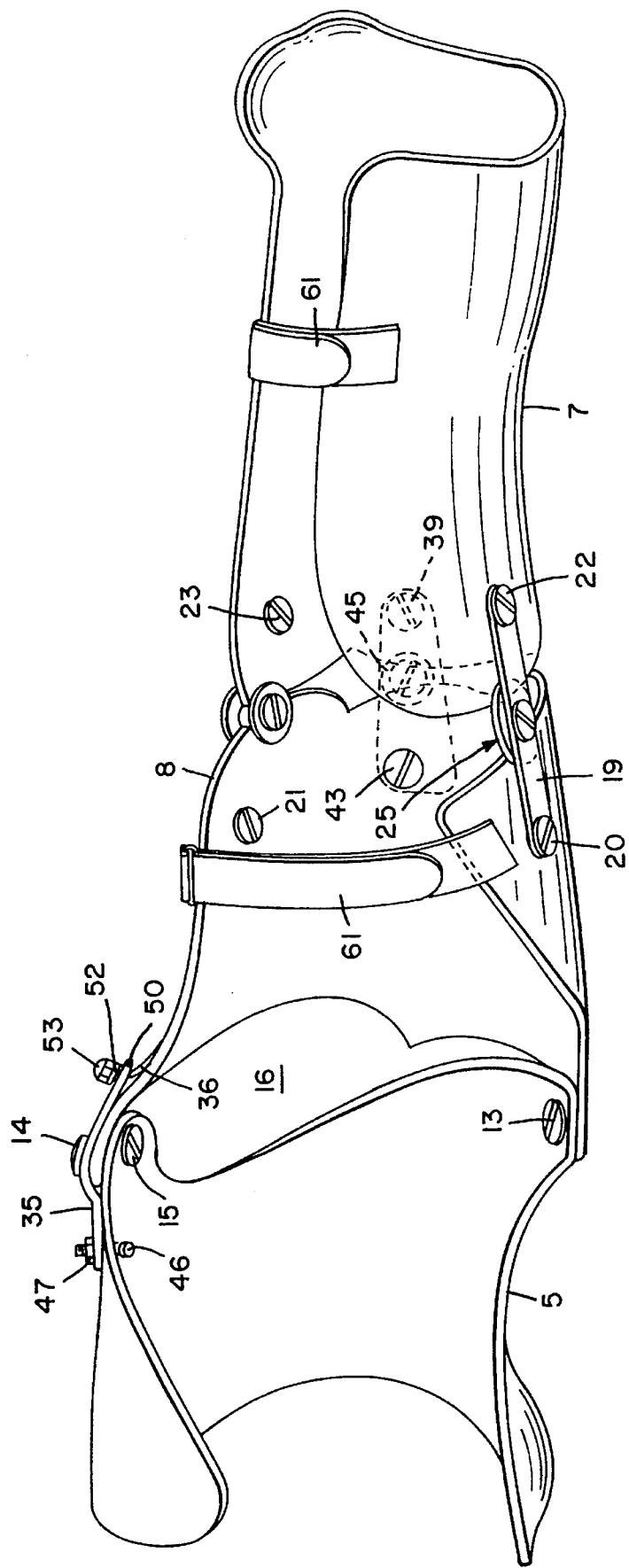
FIG. 2 is a top view of the apparatus shown in FIG. 1.
Figure 3:
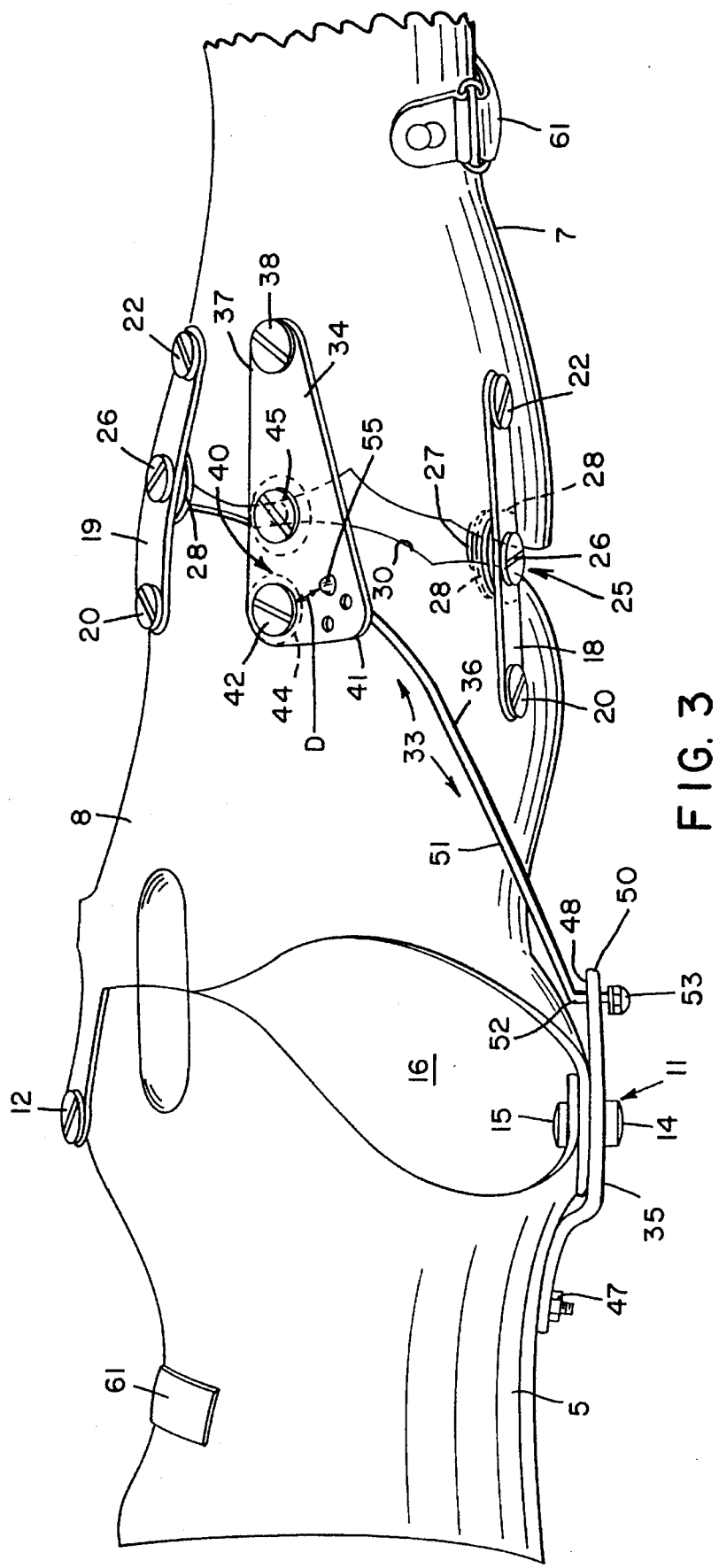
FIG. 3 is a bottom view of the apparatus shown in FIG. 1.
Figure 4:
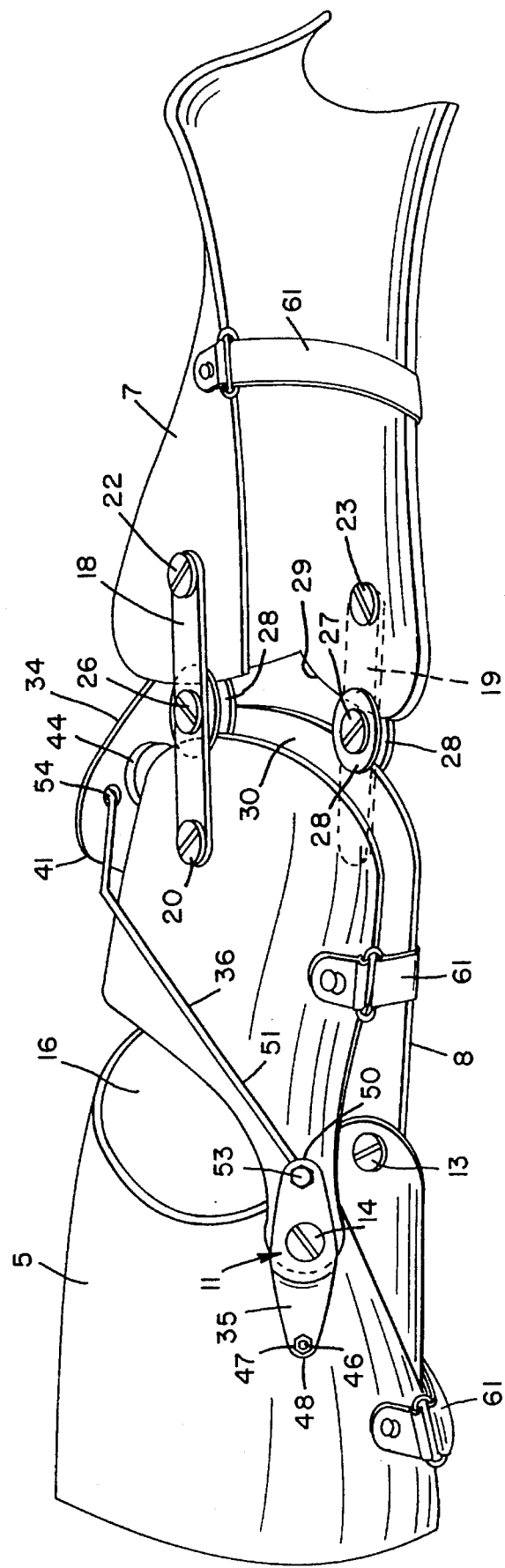
FIG. 4 is a view of one side of the apparatus in FIG. 1.
Figure 5:
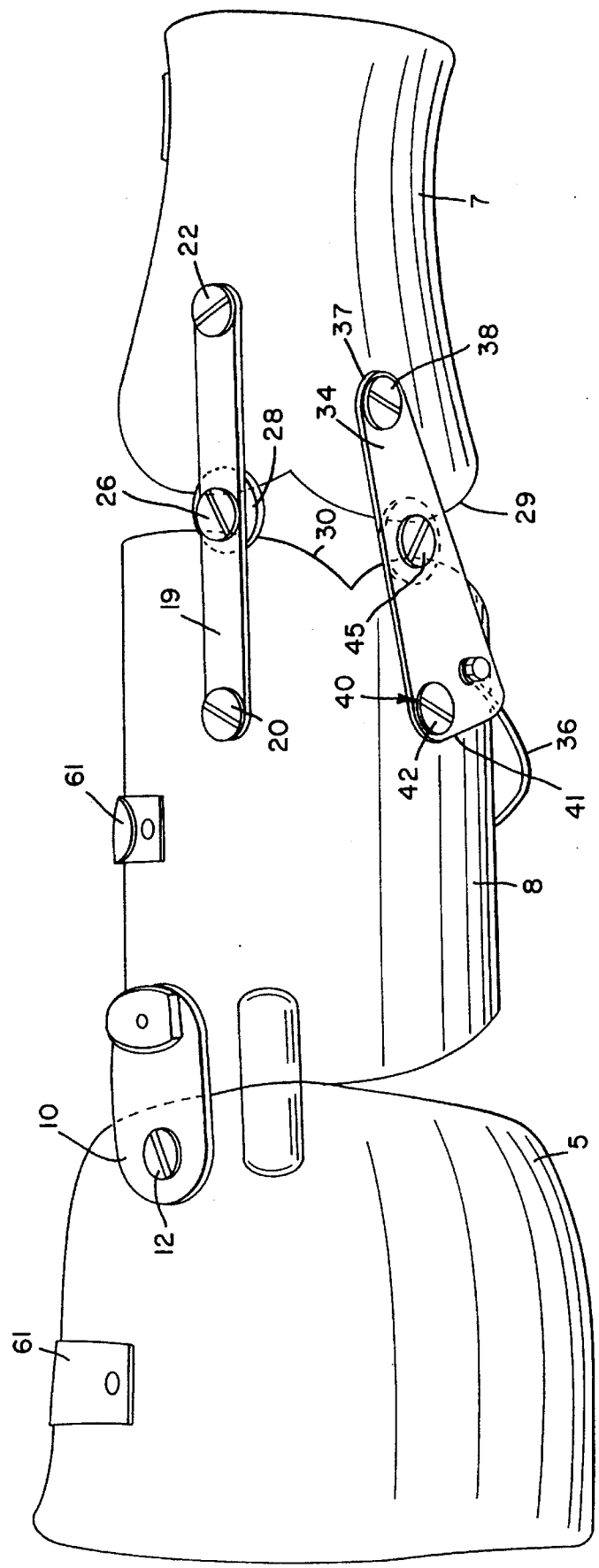
FIG. 5 is a view of the opposite side of the apparatus in FIG. 1.

The drawing shows pronation/supination apparatus 1 for orthotics and for imparting therapy, e.g., continuous passive motion, that rotates a non-functioning human wrist 2 medially and laterally about the longitudinal axis of the arm when an elbow 3 is flexed or straightened. A humeral cuff 5 receives the supper arm 6 above the elbow, a distal forearm cuff 7 receives the wrist 3 and may extend to the palmar arch, and a proximal forearm cuff 8 receives the forearm 9 between the cuffs 5 and 7, below elbow 3.

Humeral cuff 5 and proximal forearm cuff 8 are hinged to each other at 10 and 11 to permit movement when elbow 3 is flexed and extended, preferably at least ninety degrees of movement. A bolt 12 passing through cuffs 5 and 8 and bushing nut 13 provide hinge means at 10, and a bolt 14 and bushing nut 15 provide the hinge means at 11. The edges of cuffs 5 and 8 are curved away from each other between hinge means 10 and 11 to define an opening 16 for the wearer's elbow.

Proximal forearm cuff 8 and distal forearm cuff 7 are connected by an elongate flexible medial stay 18 and an identical lateral stay 19 that permit rotation of cuff 7 with respect to cuff 8, and preferably about ninety degrees of rotation. One end of each stay is pivotally connected to cuff 8 by a nut 20 and a bolt bushing 21, and the opposite end of each stay is pivotally connected to cuff 7 by a nut 22 and a bushing bolt 23. A pair of identical bushings 25 at about the center of stays 18 and 19 guide the rotational movement of distal forearm cuff 7. Each bushing may employ a nut 26 and a bolt 27 that hold a pair of flexible plastic guide washers 2 on opposite surfaces of the adjacent cuffs. The terminal edges of cuffs 7 and 8 are scalloped to define curved radial guide surfaces 29 and 30 that facilitate rotation of cuff 7.

Humeral cuff 5, proximal forearm cuff 8 and distal forearm cuff 7 are connected to each other by connecting linkage means that comprises leverage means 33 that causes distal forearm cuff 7 to rotate wrist 2 when elbow 3 is flexed and extended. Means 33 includes bell crank 34, lever 35 and linkage means 36 connecting the bell crank to the lever. One end 37 of bell crank 34 is pivotally attached to distal forearm cuff 7 by a nut 38 and a bushing bolt 39 that passes through cuff 7. The pivot axis 40 of the 9 Dell crank is located on proximal forearm cuff 8 at another end 41, and the axis is provided by nut 42 and a bushing bolt 43 that passes through the bell crank and cuff 8. A flexible washer 44 may be located between bell crank 34 and cuff 8. A guide bushing 45 that is identical to bushings 25 is located between cuffs 7 and 8 at about the center of bell crank 34. A bolt 46 passing through cuff 5 and nut 47 secure one end 48 of lever 35 to cuff 5. Bushing bolt 14 of hinge means 11 passes through lever 35, and the opposite end 50 of the lever extends over proximal forearm cuff 8 beyond where the ends of cuffs 5 and 8 are hinged to each other. Linkage means 36 may include a metal rod or link 51 that is bent to conform to the shape of cuff 8. One end 52 of rod 51 is passed up through the underside of lever end 50 and may be pivotally connected to lever 35 by a cap nut 53. Rod end 52 does not move when elbow 3 is flexed or extended. The opposite end 54 of rod 51 passes up through the underside of bell crank 34 adjacent pivot axis 40, and may be pivotally connected to the bell crank by a cap nut 55. Rod end 54 is located between wrist 2 and elbow 3 a predetermined distance D from pivot axis 40.

When elbow 3 is flexed, rod 51 pulls on bell crank 34 and pivots its end 41 around axis 40 toward the wearer's elbow 3. This pulls crank end 37 toward 9 the open side of distal forearm cuff 7 and supinates or rotates cuff 7 outwardly in a smooth steady motion. When elbow 3 is extended, rod 51 pushes on bell crank 34 and pivots its end 41 around axis 40 away from the wearer's elbow 3. This pushes crank end 37 away from the open side of distal forearm cuff 7 and pronates or rotates cuff 7 inwardly in a smooth steady motion.

Figure 6:
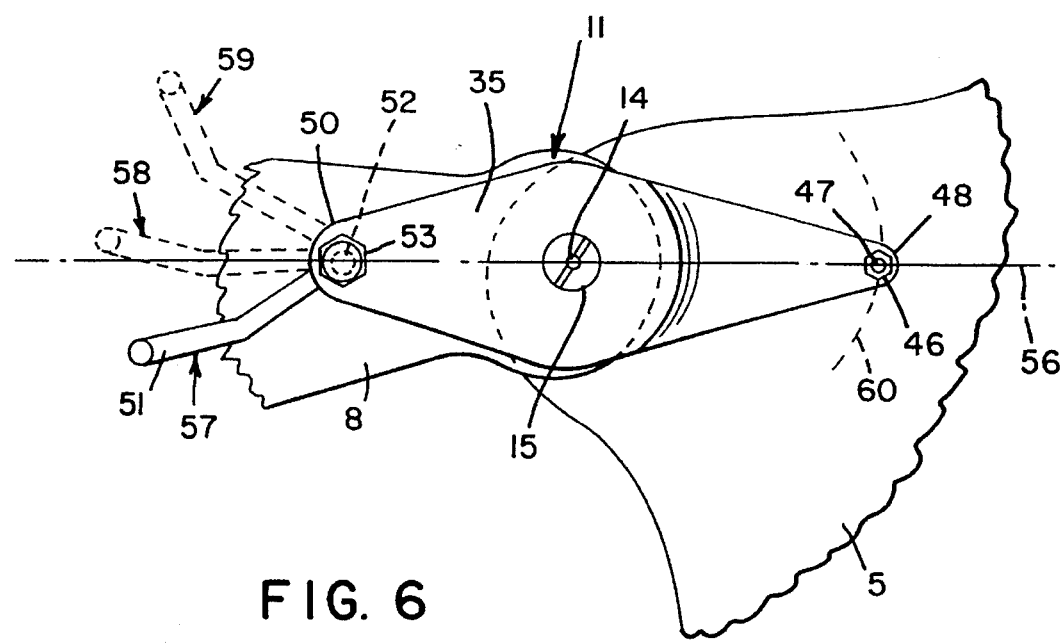
FIG. 6 is an enlarged broken away view of the lever and linkage from the embodiment of FIG. 1.

This invention permits the degree of wrist rotation and the point at which a wrist rotation begins and stops rotating to be adjusted or customized for a specific person. The degree of rotation of distal forearm cuff 7 may be varied by varying the distance D separating the point of attachment of rod end 54 and pivot axis 40. Increasing distance D will decrease the degree of rotation of cuff 7 and decreasing distance D will increase its rotation. The amount of elbow flexion that occurs before rotation begins can be varied by varying the point on humeral cuff 5 at which lever end 48 is attached. As shown in FIG. 6, bolt 46 and bushing bolt 14 and rod end 52 all lie on a common line 56 at about the center of lever 35. As rod 51 moves across line 56, the action of bell crank 34 either begins or stops. When an elbow 3 is moved from an extended position toward a flexed position, rod 51 would move from its elbow extended position 57 toward an elbow flexed position 58 where its end is approximately aligned with line 56. As rod 51 crosses line 56 moving toward another elbow flexed position 59, rotation of distal forearm cuff 7 and wrist 2 begins. As rod 51 is moved from an elbow flexed position 59 to its position 58 aligned with line 56, rotation of distal forearm cuff 7 and wrist 2 stops. The degree of elbow flexion at which wrist rotation begins and stops can be varied by changing the point at which lever end 48 is attached to humeral cuff 5. This will change the angle of line 56 with respect to rod 51 and the other components. The possible points of attachment lie on an arc 60 that has bolt 14 in hinge 11 at its center, and bolt 14 defines a turning point for pivoting end 48 and relocating bolt 47 on arc 60. Turning lever 35 so as to move bolt 47 in a clockwise direction on arc 60 will require more elbow flexion before wrist rotation begins and stops, and moving bolt 47 in a counterclockwise direction will decrease the amount of elbow flexion required.

cuffs 5, 7 and 8 may be made from a lightweight relatively rigid though flexible synthetic plastic material that can be formed or adjusted to conform to the shape of the body of the wearer. Each cuff is roughly U-shaped in cross section to permit insertion and removal of an arm and wrist. At least one hook and loop closure strap 61 should be attached to each of cuffs 5, 7 and 8 in conventional manner so that the straps span the open ends of the cuffs for holding apparatus 1 on its wearer.

Figure 10:
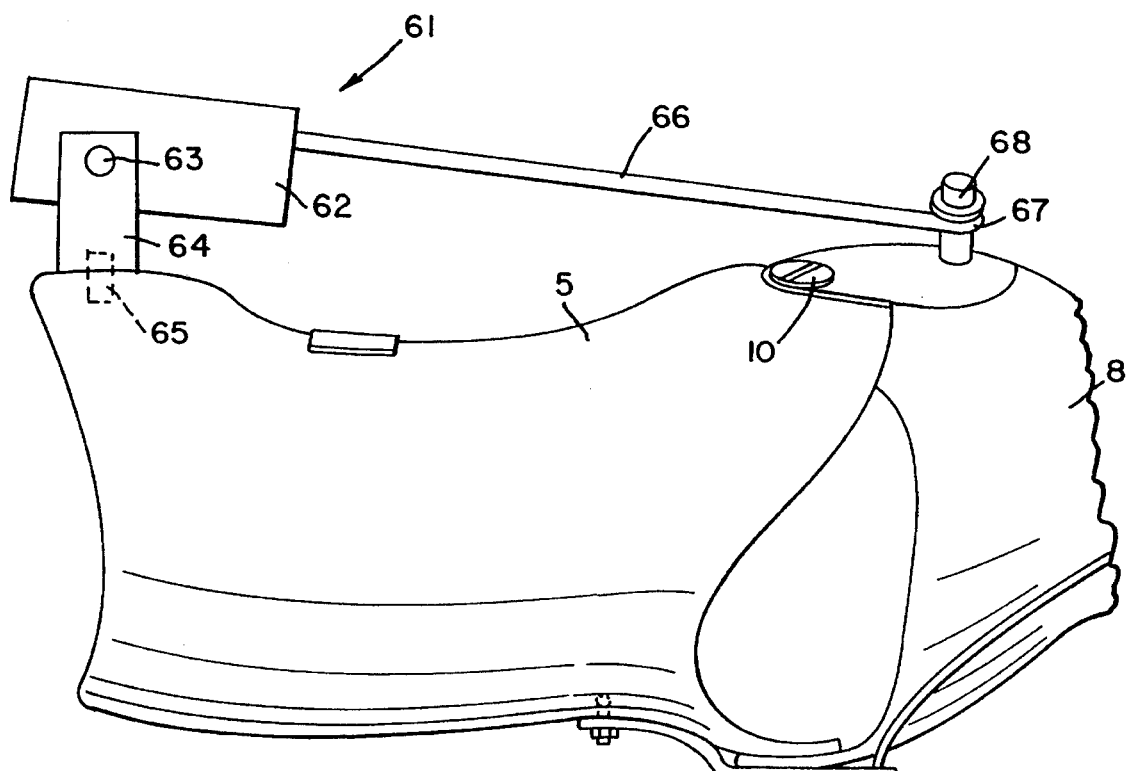
FIG. 10 is a partial bottom view corresponding to FIG. 3 of another embodiment of the invention.
Figure 7:
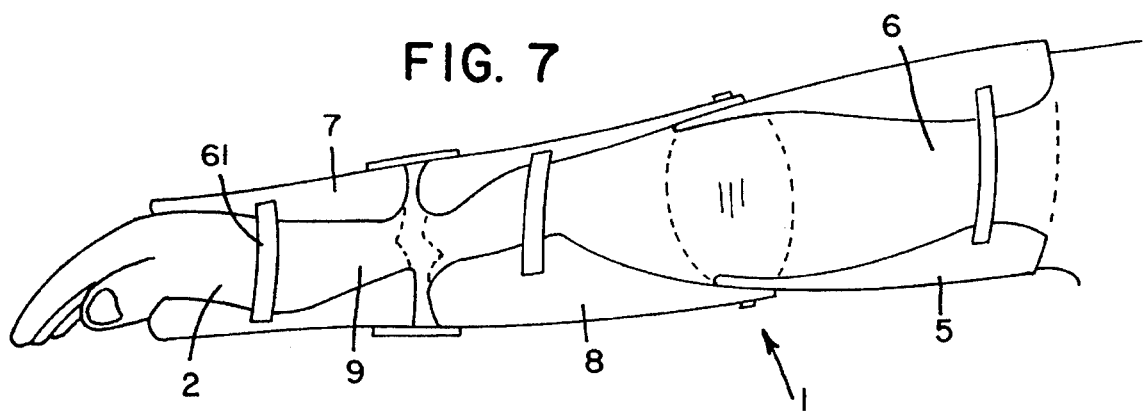
FIG. 7 is a view of the embodiment of FIG. 1 on an arm with the elbow fully extended.
Figure 8:
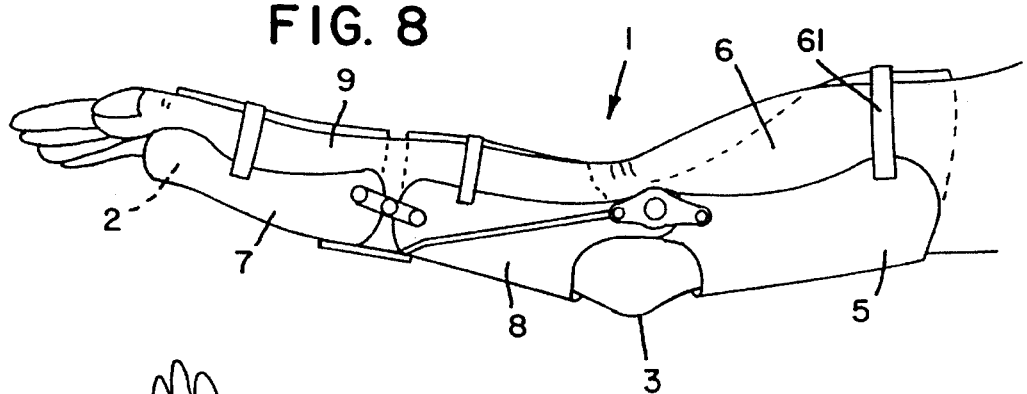
FIG. 8 is a view corresponding to FIG. 7 with the elbow partially flexed.
Figure 9:
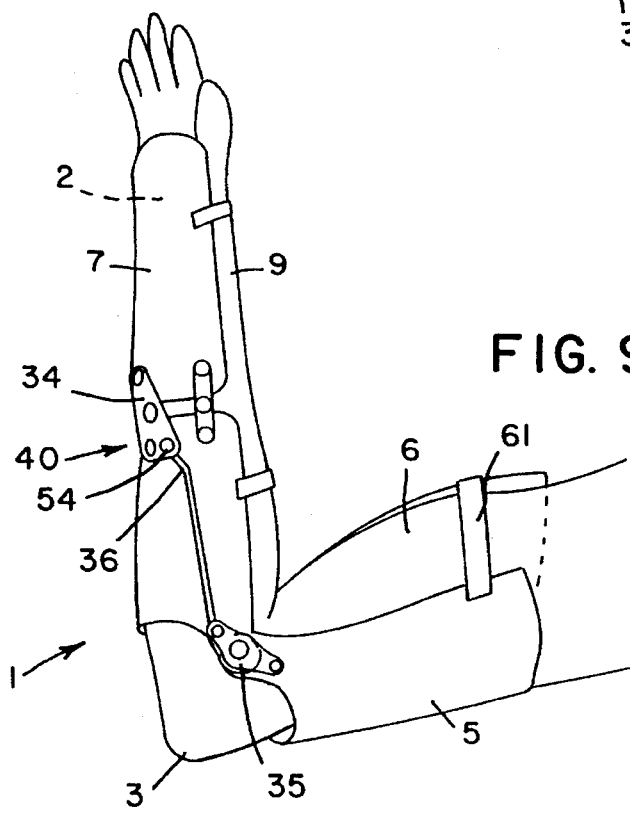
FIG. 9 is a view corresponding to FIGS. 7 and 8 with the elbow essentially fully flexed.
Figure 11:
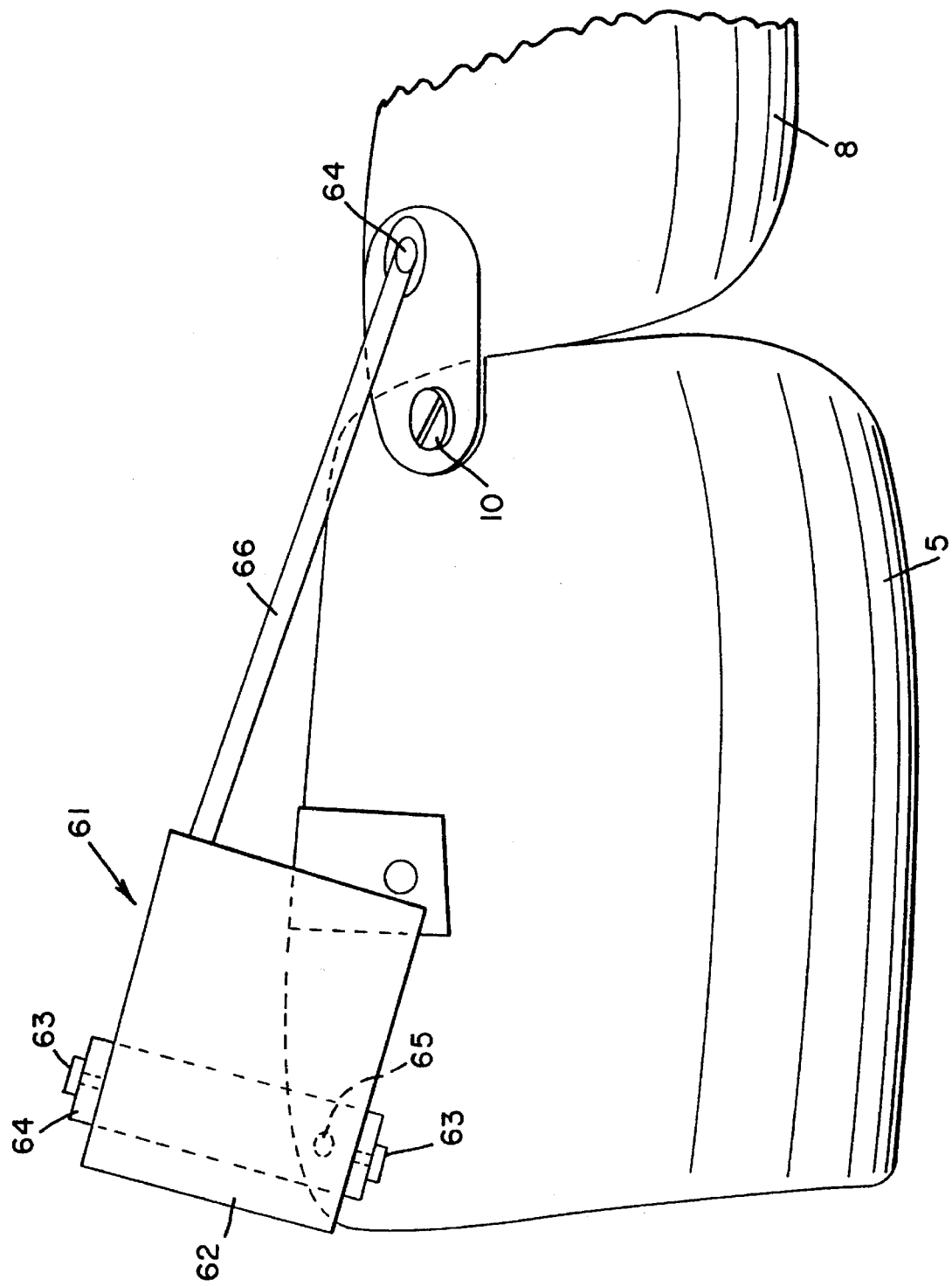
FIG. 11 is a partial side view corresponding to FIG. 5 of the embodiment of FIG. 10.

FIGS. 10 and 11 show another embodiment of the invention that may be used by a person is not able to flex or extend an elbow. This embodiment is identical in all respects to the embodiment set forth in FIGS. 1–9, except that motorized means 61 has been added for causing an elbow to flex and extend. Motorized means 61 may be an electronic range of motion apparatus as disclosed in U.S. application for patent Ser. No. 07/301,539, filed Jan. 24, 1989, and shown in FIGS. 7 and 8 thereof. The electronic range of motion apparatus has an actuator 62 that may be pivotally attached at one end by bolts 63 to a gimbal bracket 64. A bolt 65 holds bracket 64 on humeral cuff 5 and permits forward and backward rotation of the bracket. A ram 66 extends from actuator 62 and has its end 67 pivotally attached to a lug 68 that has been secured to proximal forearm cuff 8 adjacent to hinge 10. When actuator 62 pulls ram end 68 in toward the actuator, the cuffs 7 and 8 pivot toward cuff 5, and apparatus 1 functions as described when the wearer flexes elbow 3. When actuator 62 pushes ram end 68 away from the actuator, cuffs 7 and 8 pivot away from cuff 5, and apparatus 1 functions as described when the wearer extends elbow 3.

FIGS. 12–20 show another embodiment of pronation/ supination apparatus 70 for othotics and continuous passive motion that rotates a non-functioning wrist 2 medially and laterally about the longitudinal axis of the arm when an elbow 3 is flexed or straightened. Humeral cuff means 71 for attachment to an arm above the elbow comprises a humeral strut 72 having one or more cuffs 73 attached thereto. Each cuff 73 comprises a metal band 74 attached to strut 72 by screws 75 and an overlying hook and loop closure strip 76 that encircles the arm of the wearer. Each strip 76 may pass through a ring 78 attached to strut 72 before being folded back into arm holding engagement with itself. Forearm cuff means 80 for attachment to the arm below the elbow and above the wrist comprises a strut 81 having one or more cuffs 82 attached thereto. Each cuff 82 may be identical to the previously described cuffs 73. Struts 72 and 81 are hinged at 83. End 84 of strut 72 may be bifurcated and may receive end 85 of strut 81. A hinge pin 86 passing through holes in ends 84 and 85 may have flattened surfaces that abut at 87 to limit extension of the wearer's arm. Strut 81 has a right circular cylindrical rod 88 attached to its opposite end 89 by screws 90 that pass through flatened surfaces 91 on the proximal aspect of the rod.

Wrist rotation means 92 for attachment to a wearer's wrist is connected to strut 81 at end 89. Wrist rotation means 92 comprises a right circular cylindrical open-ended tube 93 having a metal band 94 secured to one end by suitable means such as welding. An overlying hook and loop closure strip 95 for encircling the hand of the wearer is attached to band 94. Tube 93 is rotatably held on strut 81 by a bolt 96 which passes through a slot 97 in the tube and is threaded into cylindrical rod 88. Slot 97 extends about 180 degrees around the circumference of tube 93.

Humeral cuff means 71, forearm cuff means 80 and wrist rotation means 92 are operatively associated with each other by connecting linkage means 98 that causes wrist rotation means 92 to rotate when the wearer's elbow 3 is flexed and extended. Linkage means 98 comprises a bracket 99 immovably secured by suitable means such as rivets to strut 72 adjacent end 84, and a rod 100 is pivotally attached at one end 101 to bracket 99 by a hinge pin 102. Rod 100 is slidably linked at its other end 103 to tube 93 by a cam follower roller 104 and cylindrical lug 105. Roller 104 and lug 105 are attached to end 103 by a bolt 106. A cam groove 107 in the surface of tube 93 exposes the interior of the tube. Cam follower 104 rolls in groove 107 so as to turn tube 93 around its central axis 111 when struts 72 and 81 pivot about pin 86. Groove 107 has a pair of straight groove portions 109 and 110 on opposed surfaces of tube 93. Groove portions 109 and 110 are essentially parallel to the tube central axis 111. A connecting groove portion 112 crosses the surface of the tube and merges with groove portions 109 and 110. Groove portion 112 will be referred to as intersecting central axis 111 at a predetermined angle 113 where the approximate middle of the groove crosses the axis, since groove portion 112 can be defined by planes that intersect axis 111 at approximately the angle 113.

Figure 18:
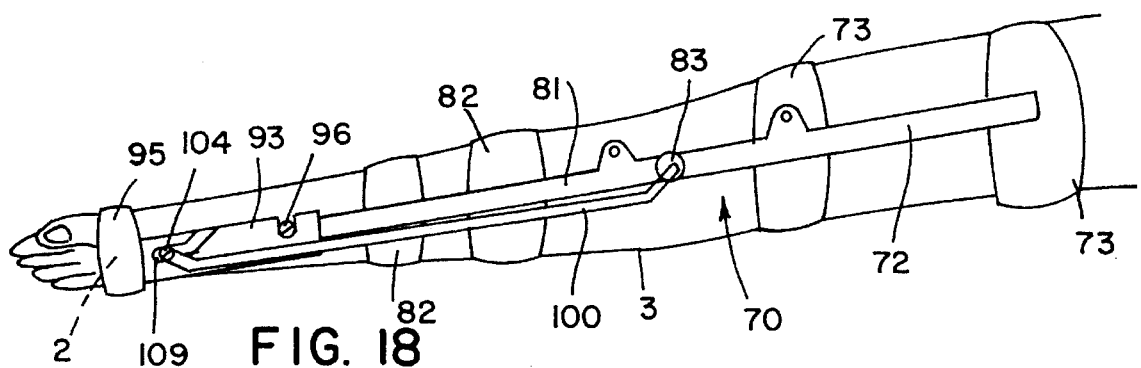
FIG. 18 is a view of the embodiment of FIG. 12 on an arm with the elbow extended.
Figure 19:
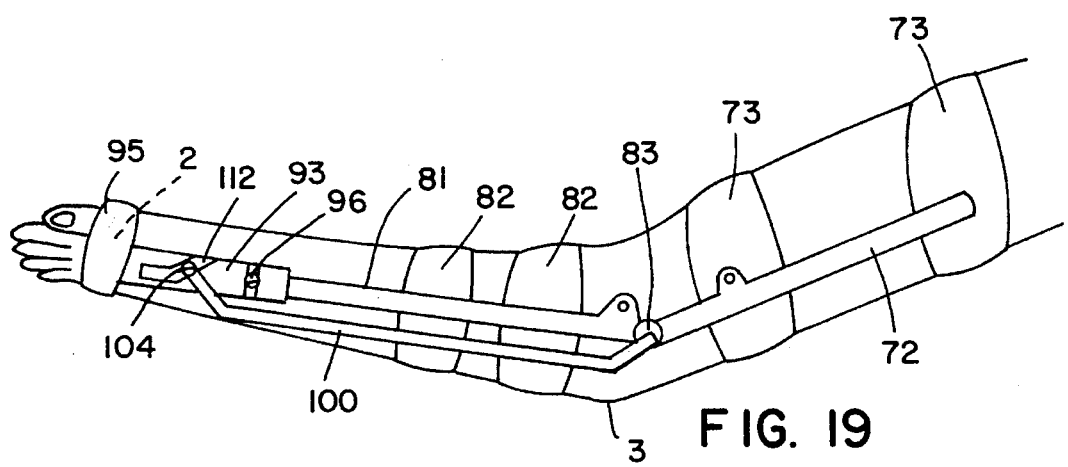
FIG. 19 is a view corresponding to FIG. 18 with the elbow partially flexed.
Figure 20:
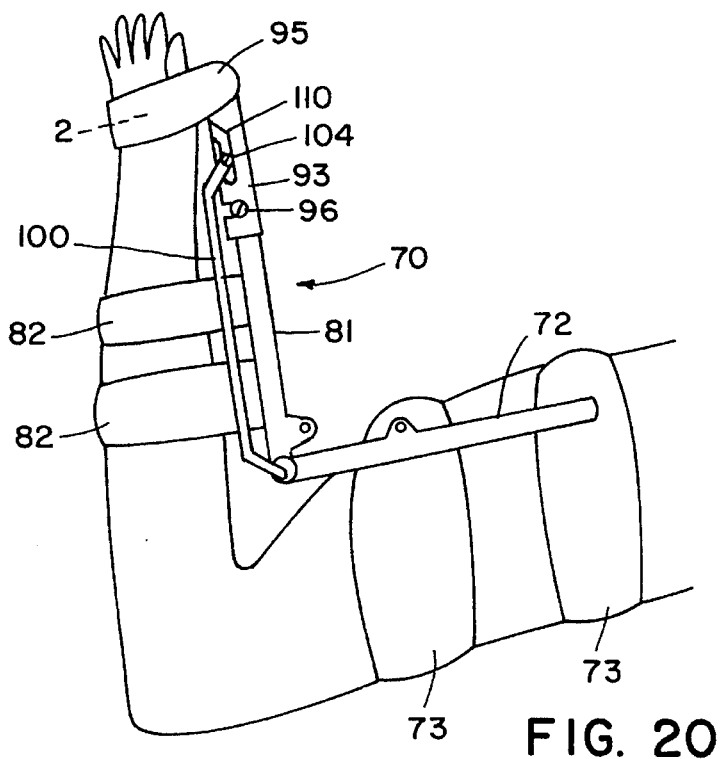
FIG. 20 is a view corresponding to FIGS. 18 and 19 with the elbow essentially fully flexed.

When the wearer's elbow is extended, as shown in FIG. 18, struts 72 and 81 are aligned and cam roller 104 is in straight groove portion 109 at its closest location to tube terminal end 114. When the elbow is partially flexed, as shown in FIG. 19, the pivoting of struts 72 and 81 toward each other draws rod 100 and cam roller 104 toward end 115 of tube 93; this causes cam roller 104 to contact connecting groove portion 112 and thereby to begin the turning of the tube 93. As the flexing of the elbow continues, cam roller 104 passes through portion 112 as the roller moves closer to end 115, and this continues to turn tube 93. When tube 93 turns in this direction, wrist rotation means 92 rotates so that the wearer's palm turns outward, away from the midline of the body. When flexing of the elbow is completed, as shown in FIG. 20, the retracting of rod 100 has drawn cam roller 104 all the way through groove portion 112 into the other straight groove portion 110. Rotation of the wrist stops when cam roller 104 is in groove portion 110. Metal band 94 and closure strip 95 rotate the hand and wrist of the wearer in the opposite direction toward the body midline when elbow 3 moves from the flexed position shown in FIG. 20 to the extended position shown in FIG. 18; this movement is caused by rotation of tube 93 by cam roller 104 as the roller moves from its position in groove portion 110 adjacent end 115 through connecting groove portion 112 and into groove portion 109 adjacent end 114.

The rate of wrist rotation and the amount of elbow flexion at which wrist rotation begins and stops can be customized for a specific person. When the angle 113 between groove portion 112 and the axis 111 of tube 93 is increased, the rate or speed at which the wrist is rotated is also increased. Decreasing the angle 113 decreases the rate at which the wrist is rotated. The amount the elbow needs to be flexed before rotation of the wrist begins is determined by the location of cam roller 104 in groove 109 or groove 110. When the elbow is extended as shown in FIG. 18, the farther the cam roller 104 is from groove portion 112, the more the elbow must flex before the wrist begins to turn, since cam roller 104 does not begin rotating tube 93 until the roller enters groove 112. Similarly, when the elbow is flexed as shown in FIG. 20, the farther the cam roller 104 is from groove portion 112, the more the elbow must be extended before the wrist begins to turn. Thus by changing the location of the cam roller 104 in groove portions 109 and 110, and by changing the angle 113 at which groove portion 112 intersects axis 111, each wearer's specific needs can be met.

Figure 21:
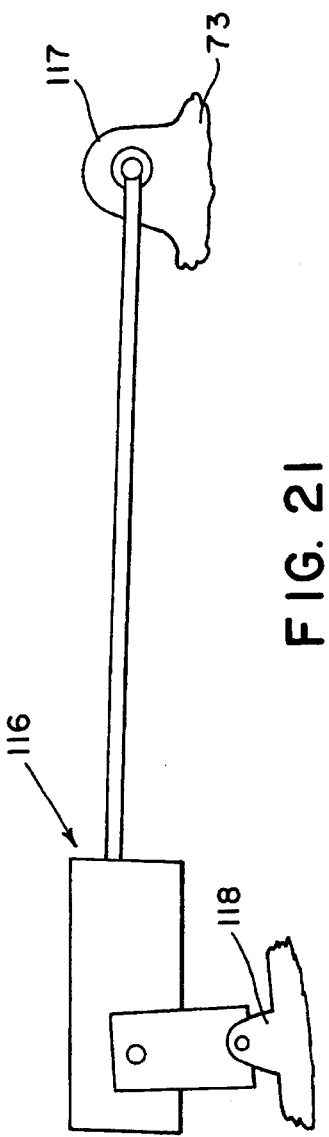
FIG. 21 is an alternative embodiment corresponding to the embodiment of FIGS. 10 and 11.
Figure 12:
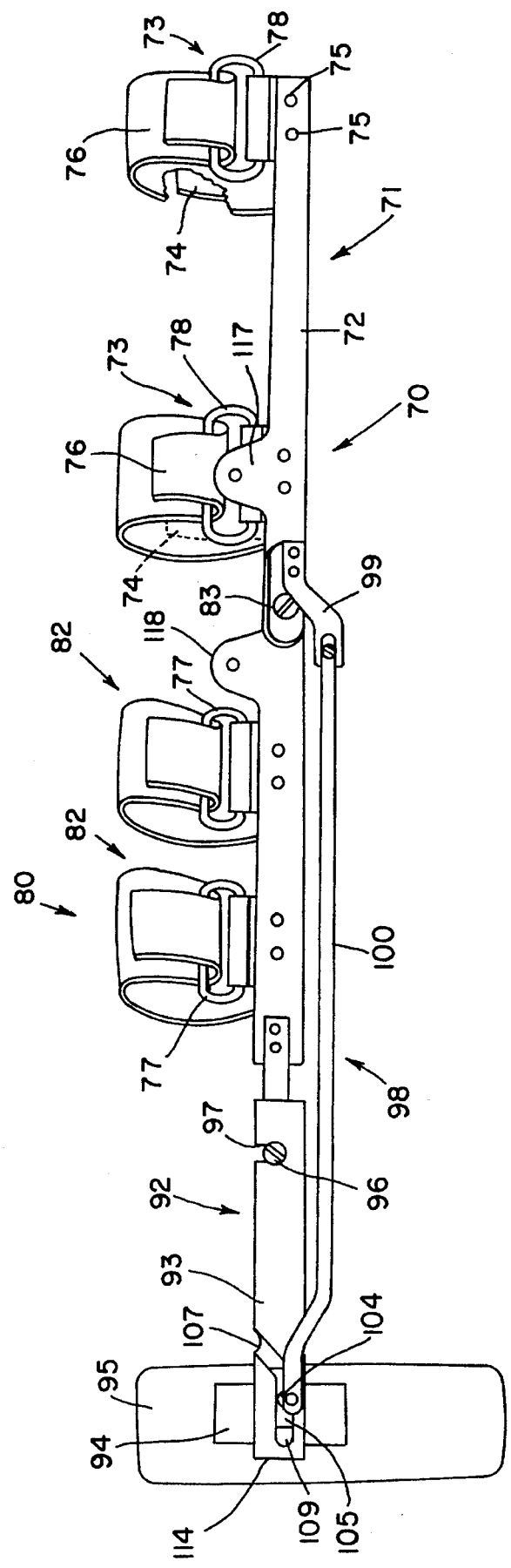
FIG. 12 is a schematic representation of another embodiment of the invention.

FIG. 21 shows another embodiment of the invention corresponding to the embodiment of FIGS. 10 and 11 that may be used by a person who can not flex or extend an elbow. The motorized means 116 is identical to that described with respect to FIGS. 10 and 11. Motorized means 116 may be pivotally and swivelly mounted in any conventional manner between an ear 117 on humeral cuff means 71 and an ear 118 on forearm cuff means 80. Motorized means 116 functions to pivot forearm cuff means 80 toward and away from humeral cuff means 71 in the same way as does means 61 when described with reference to FIGS. 1–9.

This invention also includes methods of rotating a wrist 2 of a human arm by attaching distal forearm cuff means 7 and wrist rotation means 92 to wrist 2, attaching humeral cuff means 5 and 71 to the arm above elbow 3, and attaching forearm cuff means 8 and 80 to the arm below elbow 3 between the distal forearm cuff means or wrist rotation means and the humeral cuff means. Hinging of humeral cuff means 5 and 71 and forearm cuff means 8 and 80 to each other at 10 and 11 and at 83, respectively, enables cuffs means 5 and 71 and 8 and 80 to pivot when elbow 3 is flexed and extended. Distal forearm cuff means 7 and wrist rotation means 92 are connected to forearm cuff means 8 and 80 so that cuff means 7 and means 92 can rotate relative to cuff means 8 and 80. The operative linking of all the cuff means and wrist rotation means to each other is accomplished through the use of means including linkage means 6 and 98 in such a manner that distal forearm cuff means 7 and wrist rotation means 92 rotate when elbow 3 is flexed and extended. Changing the angle 113 at which the groove portion 112 of distal cuff means 92 intersects axis 111 changes the rate at which the wrist is turned; the larger the angle 113 the faster the wrist rotates. Connecting distal forearm cuff means 7 and proximal forearm cuff means 8 with a bell crank 34 that has its pivot axis 40 on cuff 8 enables varying of the degree a wrist 2 is turned by apparatus 1. This is accomplished by varying the distance D between the end 54 of link 36 and pivot axis 40. Moving end 54 closer to axis 40 increases the amount of outward wrist rotation, and moving end 54 and axis 40 apart decreases the outward wrist rotation. The degree of elbow flexion at which rotation of wrist 2 begins and ends can be adjusted by changing the location on humeral cuff means 5 at which end 48 of leverage means 33 is connected, and by changing the location of cam roller 104 in the groove portions 109 and 110 of wrist rotation means 92.

It has thus been shown that by the practice of this invention apparatus and methods of turning a non-functioning wrist 2 when an elbow 3 is flexed or straightened can be customized to an individual's needs and adjusted as the needs change. Cumbersome springs, threaded cables and other mechanisms are not required, and apparatus embodiments 1 and 70 are sufficiently compact that a shirt can be worn over them. The use of connecting linkage means 33 and 98 results in smooth steady rotation of wrist 2 commensurate with the flexing of elbow 3 rather than jerky or uneven rotation resulting from spring mechanisms that may snap into action. External actuators such as 62 and 116 are easily attached permitting use of apparatus 1 and 70 by persons not having a functioning elbow 3.

While the invention has been described with reference to particular embodiments, it is not intended to illustrate or describe herein all of the equivalent forms or ramifications thereof. Also, the words used are words of description rather than limitation, and various changes may be made without departing from the spirit or scope of the invention disclosed herein. It is intended that the appended claims cover all such changes as fall within the true spirit and scope of the invention.

What is claimed is:

1. Apparatus for rotating a human wrist about the longitudinal axis of an arm, comprising:
   A. means for attachment to the arm above the elbow;
   B. means for attachment to the arm below the elbow and above the wrist and pivotally connected to said means for attachment to the arm above the elbow;
   C. rotatable means for attachment to the wrist; and
   D. connecting said means for attachment to the arm below the elbow to said rotatable means for causing said rotatable means to rotate the wrist when the elbow is flexed or extended.

2. The invention defined in claim 1, wherein said connecting means is pivotally attached to said means for attachment above the elbow.

3. The invention defined in claim 1, wherein said connecting means is slidably attached to said rotatable means.

4. The invention defined in claim 1, wherein said rotatable means comprises a cylindrical tube.

5. The invention defined in claim 4, wherein said tube has one end rotatably connected to said means for attachment to said arm below the elbow and above the wrist.

6. The invention defined in claim 5, wherein said tube has a cam groove exposing its interior, and cam means attached to said connecting means engages said groove.

7. The invention defined in claim 6, wherein said cam means comprises lug means slidable inside of said tube and cam follower means that rides said groove.

8. The invention defined in claim 4, wherein said means for attachment below the elbow and above the wrist extends into one end of said tube so as to rotatably support said tube.

9. The invention defined in claim 8, wherein said tube has a circumferential slot adjacent said one end, and a pin extends through said slot from said means for attachment below the elbow and above the wrist.

10. The invention defined in claim 1, further comprising electronic range of motion apparatus having an actuator movable over a range of positions, said actuator having one end connected to said means for attachment above the elbow and an opposite end connected to said means for attachment below the elbow and above the wrist for causing flexing or extension of the elbow joint.

11. The invention defined in claim 1, wherein said connecting means comprises cam means for rotating the wrist when the elbow is flexed.

12. The invention defined in claim 11, wherein said cam means comprises rotatable means having a cam groove.

13. The invention defined in claim 12, wherein said rotatable means rotates about its central axis, and said cam groove is in a plane that intersects said axis at a predetermined angle.

14. The invention defined in claim 13, wherein the rate at which the wrist is turned by said rotatable means is controlled by the angle at which said cam groove intersects said axis.

15. Apparatus for rotating a human wrist about the longitudinal axis of an arm comprising:
   A. rotatable means for attachment to the wrist;
   B. means for attachment to the arm below an elbow and above the wrist;
   C. means for attachment to the arm above the elbow; and
   D. means for causing rotation of the wrist when the elbow is flexed or extended, comprising:
      1. said rotatable means having one end rotatably connected to said means for attachment to the arm below the elbow and above the wrist;
      2. linkage means having one end pivotally attached to said means for attachment to the arm above the elbow; and
      3. cam means connected to an opposite end of said linkage means, said cam means moving along a cam surface of said rotatable means for turning said rotatable means when the elbow is flexed.

16. The invention defined in claim 15, wherein said rotatable means turns about its central axis, and said cam surface comprises a cam groove in a plane that intersects said axis at a predetermined angle.

17. The invention defined in claim 16, wherein the rate at which the wrist is turned by said rotatable means is controlled by the angle at which said cam groove intersects said axis.

18. The invention defined in claim 15, wherein said rotatable means comprises a cylindrical tube and said cam surface comprises a groove that exposes the interior of said tube.

19. The invention defined in claim 18, wherein said groove comprises a pair of substantially straight groove portions that are essentially parallel to the central axis of said tube and a spiral groove portion connecting said straight groove portions, said spiral groove portion being in a plane that intersects said axis, said cam means comprises lug means slidable inside of said tube and cam follower means that rides in said groove, said tube has a circumferential slot adjacent said one end, and a pin extends through said slot from said means for attachment to the arm below the elbow and above the wrist.

20. The invention defined in claim 19, wherein the amount of flexing or extending of the elbow required before the wrist begins to rotate can be varied by varying the location of said cam follower means in said straight groove portions.

21. The invention defined in claim 15, further comprising electronic range of motion apparatus having an actuator movable over a range of positions, said actuator having one end connected to said means for attachment above the elbow and an opposite end connected to said means for attachment below the elbow and above the wrist for causing flexing or extension of the elbow.

22. The method of rotating a wrist about the longitudinal axis of a human arm, comprising the steps of:
   A. attaching wrist rotation means to the wrist;
   B. attaching humeral cuff means to the arm above its elbow;
   C. attaching forearm cuff means to said arm below the elbow between said wrist rotation means and said humeral cuff means;
   D. hinging said humeral cuff means to said forearm cuff means so that said humeral and forearm cuff means pivot when the elbow is flexed or extended;

E. connecting said forearm cuff means to said wrist rotation means so that said wrist rotation means can rotate relative to said forearm cuff means; and F. linking said cuff means and wrist rotation means to each other in such a manner that said wrist rotation means rotates the wrist when the elbow is flexed or extended.

23. The invention defined in claim 22, further comprising linking said wrist rotation means to said forearm cuff means with tube means mounted on said forearm cuff means for rotation about the central axis of the tube means.

24. The invention defined in claim 23, further comprising rotating said tube means with cam means that moves in a cam groove in said tube means that intersects said central axis at a predetermined angle.

25. The invention defined in claim 24 further comprising varying the rate at which the wrist is rotated when the elbow is flexed or extended by changing said angle.

26. The invention defined in claim 24, further comprising varying the amount of flexion or extension of the elbow required before rotation of the wrist begins by changing the location of said cam means in said cam groove.

27. The invention defined in claim 22, further comprising connecting one end of an electronic range of motion actuator to said humeral cuff means, connecting the opposite end of said actuator to said forearm cuff means, and moving said actuator over a range of positions for causing flexion or extension of said elbow.

* * * * *